(12) United States Patent
Yuan et al.

(10) Patent No.: US 11,566,980 B2
(45) Date of Patent: Jan. 31, 2023

(54) PORTABLE REAL-TIME AIRBORNE FUNGI ACQUIRING AND DETECTING EQUIPMENT AND METHOD

(71) Applicant: JIANGSU UNIVERSITY, Zhenjiang (CN)

(72) Inventors: Shouqi Yuan, Zhenjiang (CN); Pan Wang, Zhenjiang (CN); Ning Yang, Zhenjiang (CN); Jiawei Shen, Zhenjiang (CN)

(73) Assignee: JIANGSU UNIVERSITY, Zhenjiang (CN)

( * ) Notice: Subject to any disclaimer, the term of this patent is extended or adjusted under 35 U.S.C. 154(b) by 0 days.

(21) Appl. No.: 17/703,718

(22) Filed: Mar. 24, 2022

(65) Prior Publication Data

US 2022/0349786 A1    Nov. 3, 2022

(30) Foreign Application Priority Data

Apr. 29, 2021   (CN) .......................... 202110472687.9

(51) Int. Cl.
*G01N 1/31* (2006.01)
*C12M 1/26* (2006.01)
(Continued)

(52) U.S. Cl.
CPC .............. *G01N 1/31* (2013.01); *C12M 1/261* (2013.01); *C12Q 1/04* (2013.01); *G01N 1/30* (2013.01);
(Continued)

(58) Field of Classification Search
None
See application file for complete search history.

(56) References Cited

U.S. PATENT DOCUMENTS

2016/0223435 A1*  8/2016  Takenaka ........... G01N 15/1463
2020/0355596 A1* 11/2020  Cai ..................... G01N 1/2273

FOREIGN PATENT DOCUMENTS

CN     106568696 A     4/2017
CN     107421934 A    12/2017
(Continued)

OTHER PUBLICATIONS

CNIPA, Notification of a First Office Action for CN202110472687.9, dated Sep. 8, 2021.
(Continued)

*Primary Examiner* — William H. Beisner
(74) *Attorney, Agent, or Firm* — WPAT, PC

(57) ABSTRACT

Portable real-time airborne fungi acquiring and detecting equipment and method are provided, the equipment includes a light source device, a manual constant-flow air pump, an impactor, an airborne fungi enrichment and dyeing device, and a fluorescence data collecting and processing device sequentially connected. The fluorescence detection technology is combined with the microparticle separation technology to develop the portable airborne fungi real-time acquiring and detecting equipment. This equipment improves the complex and extensive collection methods in conventional airborne fungi detection and the demand limitation of independent detection equipment, and realizes the real-time collection and quantification of airborne fungi concentration. Moreover, the equipment has the advantages of small volume, low costs, easy operation and is easy to be prompted.

1 Claim, 5 Drawing Sheets

(51) Int. Cl.
  *C12Q 1/04* (2006.01)
  *G01N 1/30* (2006.01)
  *G01N 21/64* (2006.01)
  *G01N 21/94* (2006.01)
  *B01L 1/00* (2006.01)

(52) U.S. Cl.
  CPC ......... *G01N 21/6428* (2013.01); *G01N 21/94* (2013.01); *B01L 1/00* (2013.01); *G01N 2021/6439* (2013.01); *G01N 2201/062* (2013.01)

(56) References Cited

FOREIGN PATENT DOCUMENTS

| | | | | |
|---|---|---|---|---|
| CN | 108009404 A | | 5/2018 | |
| CN | 111610175 A | * | 9/2020 | ............. G01N 15/10 |
| KR | 20110128743 A | * | 11/2011 | |

OTHER PUBLICATIONS

Jiangsu Univ. (Applicant), Reply to Notification of a First Office Action for CN202110472687.9 w/ Replacement Claims, dated Sep. 30, 2021.

CNIPA, Notification to grant patent right for invention for CN202110472687.9, dated Nov. 22, 2021.

* cited by examiner

```
┌─────────────────┐
│      start      │
└────────┬────────┘
         ▼
adding 20 μL of fluorescent dye to the reaction tank with
pipette gun and installing the detecting equipment as
required
         │
         ▼
shaking the piston of the manual constant-flow air pump
clockwise to the top of the pump cavity and collecting the
micro-particles in the air into the pump cavity
         │
         ▼
shaking the manual constant-flow air pump
counterclockwise, and the micro-particles in the pump
cavity enter the impactor at a constant speed, so as to
separate the target fungus particles
         │
         ▼
collecting the target fungus particles into the fluorescence
reaction tank to realize the dyeing of the target fungus
particles
         │
         ▼
turning on the fluorescent light source and data colleting
and processing device, and using CMOS sensor to shoot
the image of fluorescent reaction
         │
         ▼
processing the fluorescence image by the microprocessor to
quantify the microbial particles, and saving the processed
data to the database, and the obtained images and data can
be queried directly from the display screen
         │
         ▼
┌─────────────────┐
│       end       │
└─────────────────┘
```

FIG. 8

PORTABLE REAL-TIME AIRBORNE FUNGI ACQUIRING AND DETECTING EQUIPMENT AND METHOD

TECHNICAL FIELD

The disclosure relates to the technical field of microbial detection, and in particular to a portable real-time airborne fungi acquiring and detecting equipment and method.

BACKGROUND

Microbial detection is one of the key steps in clinical diagnosis and food safety determination. With the development of microfluidic technology, microfluidic, as a micro nano fluid treatment technology, has attracted much attention in recent years. Due to the advantages of low costs, high flux, fast analysis speed and little reagent consumption, microfluidics/microfluidic technology is of great significance for reducing the cost of fungi and bacterial detection system, and realizing small integrated equipment.

At present, the research on the real-time airborne fungi acquisition and detection technology is in its infancy. Chinese patent application No. CN201711321042.5 (corresponding to Chinese paten publication No. CN108009404A) discloses Detection Method of Environmental Microorganisms, including conventional microbial sampling, undifferentiated biological detection, data analysis and grade evaluation, which can realize noninvasive, efficient, comprehensive and accurate evaluation of biological diseases. However, this method requires professionals to operate, the environment requirements of the detection site are strict, and the required detection equipment is expensive and inconvenient to carry, which is not conducive to popularization.

SUMMARY

Aiming at the difficulty in real-time detection of airborne fungi, the disclosure provides a portable real-time airborne fungi acquiring and detecting equipment and method. The disclosure integrates immunofluorescence technology, gas micro particle separation technology and image processing technology, which can accurately detect the concentration of airborne fungi in a real-time manner. Therefore, the method has the advantages of good novelty, simple structure, convenient operation and high integration.

In order to achieve the above purposes, the disclosure provides the following schemes: a portable real-time airborne fungi acquiring and detecting equipment, includes a light source device, a manual constant-flow air pump, an impactor, an airborne fungi enrichment and dyeing device, a fluorescence data acquiring and processing device sequentially connected in that order:

the light source device includes a box body and a light-emitting component installed in the box body, the box body is provided with a light-transmitting hole; a connecting component is arranged between the manual constant-flow air pump and the box body; and the manual constant-flow air pump is connected to the light-transmitting hole through the connecting component;

the manual constant-flow air pump includes a manual driver and a constant-flow piston pump in transmission connection with the manual driver, the inlet end of the constant-flow piston pump is communicated with the connecting component, and the outlet end of the constant-flow piston pump is communicated with the impactor; valves are installed the inlet end and the outlet end of the constant-flow piston pump, and between the light-transmitting hole and the connecting component respectively; the light emitted by the light-emitting component is capable of passing through the connecting component, the constant-flow piston pump and the impactor in sequence to irradiate the airborne fungi enrichment and dyeing device.

Preferably, the light-emitting component includes a circuit fixing bracket, a white light-emitting diode, a first power supply and an excitation filter device; the white light-emitting diode is electrically connected with the first power supply through a wire, the outer side of the wire is covered with a circuit protection layer, the white light-emitting diode is fixedly matched with the circuit fixing bracket through the circuit protection layer, and the white light-emitting diode horizontally corresponds to the light-transmitting hole; a power button is connected in series on the wire, and the power button is fixed outside the box body; a shading plate is fixed on one side of the box body close to the manual constant-flow air pump, and the light-transmitting hole is arranged on the shading plate; the excitation filter device is arranged between the shading plate and the white light emitting diode; the excitation filter device includes an excitation filter holder detachably connected with the box body, the excitation filter holder is detachably connected with an excitation filter (also referred to as a color filter) and a light-transmitting protective layer, and the light-transmitting protective layer is located between the excitation filter and the shading plate.

Preferably, the connecting component includes a connecting pipe and a T-joint, one end of the connecting pipe is communicated with the light-transmitting hole, and the other end of the connecting pipe is provided with the valve, two ports in the horizontal direction of the T-joint are respectively communicated with the valve on the connecting pipe and the valve on the inlet end of the constant-flow piston pump, and a suction hose is communicated with the port in the perpendicular direction of the T-joint.

Preferably, the constant-flow piston pump includes a pump cavity, and the bottom of the pump cavity is symmetrically provided with a manual constant-flow air pump inlet channel and a manual constant-flow air pump outlet channel; the pump cavity is slidably connected with a pneumatic piston, the middle part of the top end of the pneumatic piston is fixedly connected with a pressure lever, and the manual driver is in transmission connection with the pressure lever; the inner wall of the pump cavity is fixedly connected with a limit ring, the end surface of the bottom of the limit ring is flush with the top of the manual constant-flow air pump inlet channel, and the pneumatic piston is matched with the limit ring in positionally limiting manner.

Preferably, the manual driver includes brackets symmetrically fixed outside the pump cavity; two three-way clamps are fixed at the tops of the brackets respectively, and the two three-way clamps are internally provided with a transmission shaft; a driving gear is fixed on the transmission shaft, and a pressure lever gear is fixed on the pressure lever; the driving gear is meshed with the pressure lever gear; one end of the transmission shaft is provided with a handle.

Preferably, a transmission shaft friction disk is fixed at one end of the transmission shaft; a driving friction disk is arranged at one side of the transmission shaft friction disk facing away from the three-way chuck; the driving friction disk is sleeved on the transmission shaft; a torque adjusting bolt is arranged between the driving friction disc and the transmission shaft; the driving friction disk is rotatably connected with the transmission shaft through the torque adjusting bolt; the handle is perpendicularly fixed on the side wall of the driving friction disk; the driving friction disk is in transmission match with the transmission shaft friction disk.

Preferably, the impactor includes an impactor inlet channel; one end of the impactor inlet channel close to the manual constant-flow air pump is communicated with a port; the end of the port is communicated with the valve at the constant-flow piston pump outlet end; one end of the impactor inlet channel facing away from the interface is communicated with a main airflow channel; two ends of the main airflow channel are provided with air pumps, and the middle of the main airflow channel is provided with a secondary airflow channel; the secondary airflow channel is coaxially arranged with the impactor inlet channel; the external side of the secondary airflow channel is provided with a port threaded male head; the airborne fungi enrichment and dyeing device is installed on the secondary airflow channel through the interface threaded male head.

Preferably, the airborne fungi enrichment and dyeing device includes a polymethyl methacrylate (PMMA) baseplate and a cylindrical wall fixed on the PMMA baseplate; the inner side of the cylindrical wall is provided with an interface threaded female head; the interface threaded female head is in threaded connection with the interface threaded male head; a reaction tank is fixed in the middle of the PMMA baseplate.

Preferably, the fluorescence data collecting and processing device includes a detection equipment housing, an emission filter (also referred to as a color filter) and a data display screen installed on the detection equipment housing; a connector is installed at one end of the detection equipment housing close to the emission filter, and the detection equipment housing is connected with the airborne fungi enrichment and dyeing device through the connector;

the emission filter is located between the detection equipment housing and the airborne fungi enrichment and dyeing device, a complementary metal oxide semiconductor (CMOS) image sensor is arranged between the emission filter and the detection equipment housing, and a microcontroller and a second power supply are installed in the detection equipment housing; the CMOS image sensor, the data display screen and the second power supply are electrically connected to the microcontroller, and the data display screen is fixed on the side wall of the detection equipment housing facing away from the CMOS image sensor.

A portable airborne fungi real-time acquiring and detecting method, includes:

S1. preparation: adjusting the position of the torque adjusting bolt according to the flow rate required for the separation of the detection target, adjusting the pneumatic piston to the limit ring, and adding fluorescent dye into the reaction tank with a pipette gun;

S2. assembly of detecting equipment: keeping the light-transmitting hole, manual constant-flow air pump inlet channel, manual constant-flow air pump outlet channel and reaction tank on the same horizontal line to ensure the barrier-free propagation of the light;

S3. collection and dyeing of fungus particles in the air: sending the collected air with fungus particles to the impactor at a uniform speed by a manual constant-flow air pump for separation, and enriching and dyeing the separated target airborne fungus particles in the reaction tank;

S4. detection of fungus particles in the air: after dyeing the separated fungus particles, starting the light source device to stimulate the dyed fungus particles, and starting the fluorescence data collecting and processing device to collect and process the fluorescent image after the dyeing, thereby to obtain the calculation result of microbial content in the air.

Compared with the prior art, the disclosure has the following technical effects:

1. The disclosure relates to a portable real-time acquiring and detecting equipment and method for airborne fungi. The device uses human hands as a power source to realize collection, separation and enrichment of airborne fungi, and has simple operation and strong portability.

2. The disclosure relates to a portable real-time acquiring and detecting equipment and method for airborne fungi. According to the principle of constant torque, a manual constant-flow air pump is designed for the equipment with the characteristics of adjustable flow and stable outflow, with wide outflow range, convenient flow adjustment and strong practicability.

3. The disclosure relates to a portable real-time acquiring and detecting equipment and method for airborne fungi. The equipment is designed to use the surface tension and wettability of liquid in a small space to fix fluorescent staining solution, so as to realize the dyeing of detection targets, and the equipment has small volume and low costs.

4. The disclosure relates to a portable real-time airborne fungi acquiring and detecting equipment and method. The equipment innovatively combines an impactor with a microbial staining structure detection structure, thus making the real-time detection of physical and chemical properties of airborne fungi easier.

5. The disclosure relates to a portable real-time acquiring and detecting equipment and method for airborne fungi. The equipment combines a white light emitting diode with a detachable excitation filter as a detection light source to excite monochromatic light with a specific wavelength; according to the index characteristics of the detection target, the equipment instantly selects the corresponding light source configuration, which makes the detection result of the target microorganism more accurate.

6. The disclosure relates to a portable real-time acquiring and detecting equipment and method for airborne fungi, the equipment as a whole is small, portable, easy to operate, and is conducive to commercial promotion.

BRIEF DESCRIPTION OF THE DRAWINGS

In order to more clearly explain the embodiments of the disclosure or the technical schemes in the prior art, the drawings needed in the embodiments will be briefly introduced below. Obviously, the drawings in the following description are only some embodiments of the disclosure, and for ordinary technicians in the field, other drawings can be obtained according to these drawings without paying creative efforts.

FIG. 8 is a work flow chart of a portable airborne fungi real-time acquiring and detecting equipment according to the disclosure.

In drawings, light source device—1, power button—2, excitation filter holder—3, shading plate—4, light-transmitting hole—5, connecting pipe—6, valve—7, manual constant-flow air pump inlet channel—8, manual constant-flow air pump—9, manual constant-flow air pump outlet channel—10, interface—11, impactor inlet channel—12, impactor—13, airborne fungi enrichment and dyeing device—14, connector—15, fluorescence data collecting and processing device—16, data display screen—17, box body—18, first power supply—19, circuit fixing bracket—20, circuit protection layer—21, excitation filter device—22, white light emitting diode—23, excitation filter—24, light-transmitting protective layer—25, bracket—26, three-way clamp—27, pressure lever—28, pressure lever gear—29, driving gear—30, pneumatic piston—31, pump cavity—32, transmission shaft friction disk—33, driving friction disk—34, torque adjusting bolt—35, handle—36, limit ring—37, transmission shaft—38, PDMS (Polydimethylsiloxane) film—39, PDMS film holder—40, acceleration zone—41, main airflow channel—42, secondary airflow channel—43, interface threaded male head—44, reaction tank 45, reaction tank wall—46, PMMA (polymethyl methacrylate) chassis—47, cylindrical wall—48, interface threaded female head—49, emission filter—50, CMOS (Complementary Metal Oxide Semiconductor) image sensor—51, microcontroller—52, second power supply—53, detection equipment housing—55, T-joint—56, suction hose—57.

DETAILED DESCRIPTION OF THE EMBODIMENTS

Next the technical schemes in the embodiments of the disclosure will be clearly and completely described with reference to the drawings in the embodiments of the disclosure. Obviously, the described embodiments are only part of the embodiments of the disclosure, not all of them. Based on the embodiments in the disclosure, all other embodiments obtained by ordinary technicians in the field without creative efforts are within the scope of the disclosure.

In order to make the above-mentioned objects, features and advantages of the disclosure more obvious and easier to understand, the disclosure will be described in further detail below with reference to the accompanying drawings and specific embodiments.

Figure 1:
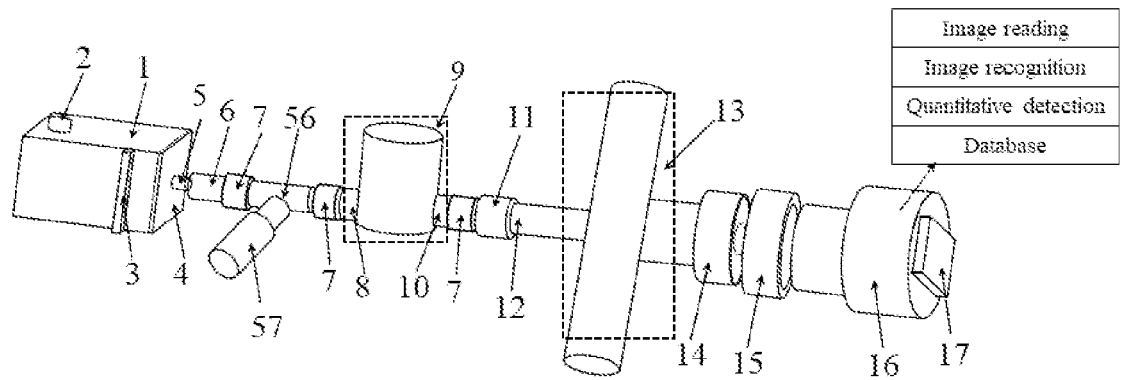
FIG. 1 is a schematic diagram of the overall structure of the portable airborne fungi real-time acquiring and detecting equipment of the disclosure.
Figure 2A:
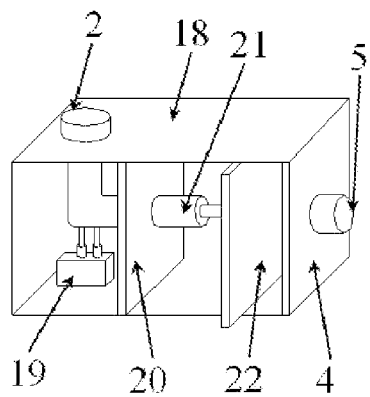
FIG. 2A is a three-dimensional view of the internal structure of the light source device.
Figure 2B:
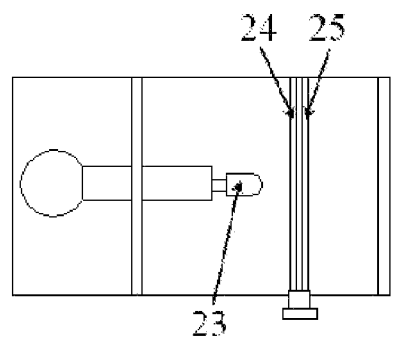
FIG. 2B is a top view of the internal structure of the light source device.
Figure 2C:
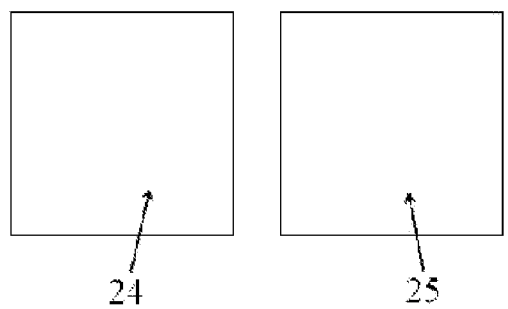
FIG. 2C is a schematic diagram of the excitation filter and the light-transmitting protective layer of the internal structure of the light source device.

Referring to FIG. 1, a portable airborne fungi real-time acquiring and detecting equipment provided by the disclosure includes a total of nineteen components, i.e., a light source device 1, a power button 2, a excitation filter holder 3, a shading plate 4, a light-transmitting hole 5, a connecting pipe 6, valves 7, a manual constant-flow air pump inlet channel 8, a manual constant-flow air pump 9, a manual constant-flow air pump outlet channel 10, an interface 11, an impactor inlet channel 12, an impactor 13, an airborne fungi enrichment and dyeing device 14, a connector 15, a fluorescence data collecting and processing device 16, a data display screen 17, a T-joint 56, and a suction hose 57. The light source device 1 provides light signal with specific wavelength for the fluorescence reaction of airborne fungi enrichment and dyeing device 14 to promote the generation of fluorescence reaction; one end of connecting pipe 6 is connected to the light-transmitting hole 5 on the shading plate 4, and the other end is connected to the valve 7, the valve 7 is always closed during the work of the equipment to ensure that there is no external environmental interference at the light source device 1; the manual constant-flow air pump inlet channel 8 and manual constant-flow air pump outlet channel 10 are connected to valves 7, which is used to control the inlet and outlet state of manual constant-flow air pump 9; the T-joint 56 is placed between the light source device 1 and the manual constant-flow air pump 9, and one port of the symmetrical ports at both two ends is connected to valve 7 on connecting pipe 6, and the other port is connected to valve 7 on manual constant-flow air pump inlet channel 8, so as to ensure the straight line propagation of light inside the channel; the port in the perpendicular direction of the T-joint 56 is connected to the suction hose 57 for the collection of microbial particles in the air; the manual constant-flow air pump 9 is connected to the impactor inlet channel 12 through the interface 11, and the airborne fungi enrichment and dyeing device 14 is installed at the end of the impactor 13; the airborne fungi enrichment and dyeing device 14 is connected to the fluorescence data collecting and processing device 16 through the connector 15; the fluorescence data collecting and processing device 16 is mainly used for collecting and processing fluorescence images, quantitative analysis of test results and storing test data; at the same time, the data display screen 17 can also directly read the test results, which is convenient for the user.

With reference to FIG. 1 and FIGS. 2A-2C, the light source device 1 includes a total of eleven components, i.e., a power button 2, a shading plate 4, a light-transmitting hole 5, a box body 18, a first power supply 19, a circuit fixing bracket 20, a circuit protection layer 21, an excitation filter device 22, a white light-emitting diode 23, an excitation filter 24, and a light-transmitting protective layer 25. The first power supply 19 is a 5V power supply, and the first power supply 19 supplies power to the white light-emitting diode 23; the setting of the circuit protection layer 21 can protect the circuit centrally to ensure the safety of the power supply device; the excitation filter device 22 includes three components: an excitation filter holder 3, an excitation filter 24 and a light-transmitting protective layer 25; the three components are placed between the white light-emitting diode 23 and the shading plate 4; in addition, the placement height of white light-emitting diode 23 is level with the light-transmitting hole 5; the excitation filter 24 is used to select the characteristic waveband spectral signal for excitation fluorescence; the setting of excitation filter holder 3 can realize the real-time replacement of excitation filter 24 and light-transmitting protective layer 25 to realize the supply of multiple characteristic wavelengths in the system; the addition of light-transmitting protective layer 25 can reduce the contamination of excitation filter 24.

Figure 3:
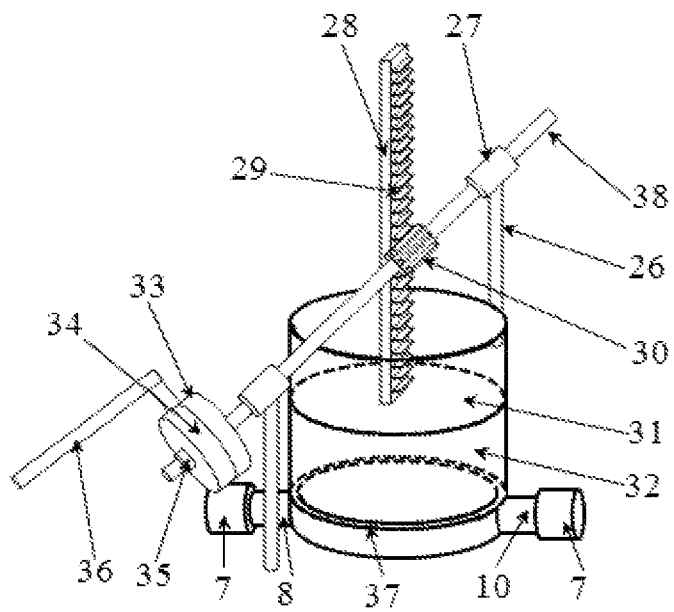
FIG. 3 is a schematic structural diagram of a manual constant-flow air pump in the disclosure.

With reference to FIG. 1 and FIG. 3, the manual constant-flow air pump 9 includes eighteen parts, i.e., valves 7, a manual constant-flow air pump inlet channel 8, a manual constant-flow air pump outlet channel 10, a transmission shaft 38, bracket 26, a three-way clamp 27, a pressure lever 28, a pressure lever gear 29, a driving gear 30, a pneumatic piston 31, a pump cavity 32, a transmission shaft friction disk 33, a driving friction disk 34, a torque adjusting bolt 35, a handle 36, a limit ring 37, a PDMS film 39, and a PDMS film holder 40. The transmission shaft 38 and the bracket 26 are combined together through the three-way clamp 27; the transmission shaft 38, the pressure lever 28, the pressure lever gear 29, the driving gear 30, the pneumatic piston 31, the transmission shaft friction disk 33, the driving friction disk 34, the torque adjusting bolt 35 and the handle 36 form the main body of the driving device; the pressure lever 28 is connected to the center of the pneumatic piston 31 and is located directly above the pneumatic piston 31; the pressure lever gear 29 is located on the surface of the pressure lever 28; the driving gear 30 is located on the surface of the transmission shaft 38 and meshed with the pressure lever gear 29 to drive the pneumatic piston 31 up and down; the transmission shaft friction disk 33 and the transmission shaft 38 are an integrated structure; the handle 36 is fixed vertically on the side of the driving friction disk 34, and the driving friction disk 34 is closely placed with the transmission shaft friction disk 33, and the manual constant-flow air pump 9 uses the friction between the driving friction disk 34 and the transmission shaft friction disk 33 to drive driving friction disk 34 rotate and realize the pneumatic piston 31 move up and down. When the friction between the driving friction disk 34 and the transmission shaft friction disk 33 is in static friction, the flow rate of the manual constant-flow air pump 9 (i.e., the speed of the up-and-down movement of the pneumatic piston 31) increases with the increase of the external force on the handle 36; when the friction force between the driving friction disk 34 and the transmission shaft friction disk 33 exceeds the maximum static friction, the friction force between the driving friction disk 34 and the transmission shaft friction disk 33 is sliding friction, the flow rate of the manual constant-flow air pump 8 will not change with the change of the external force on the handle 36, and at this time, the manual constant-flow air pump 8 flow output will be in a constant state; the torque adjusting bolt 35 is used to adjust the torque between the driving friction disk 34 and the transmission shaft friction disk 33, which determines the final working flow rate of the manual constant-flow air pump 9; the limit ring 37 is set directly above the manual constant-flow air pump inlet channel 8 and the manual constant-flow air pump outlet channel 10, which marks the lowest position of the pump cavity 32 that can be reached by the pneumatic piston 31; the top of the pump cavity 32 is the highest position that can be reached by the pneumatic piston 31; the manual constant-flow air pump inlet channel 8 and the manual constant-flow air pump outlet channel 10 are symmetrically set at the top of the pump cavity 32. air pump outlet channel 10 are symmetrically provided on both sides of the bottom of the pump cavity 32, and both are connected with valves 7 for controlling the inlet and outlet flow status of the manual constant-flow air pump 8.

Figure 7A:
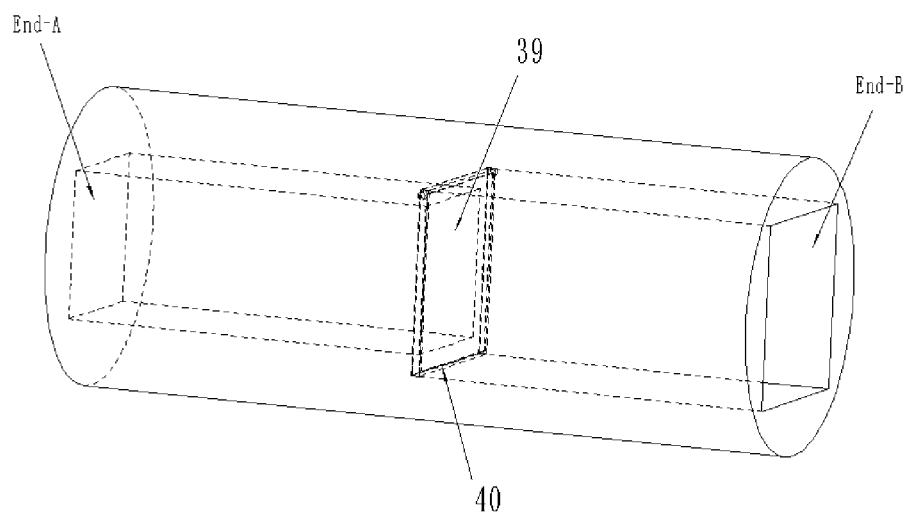
FIG. 7A is the schematic diagram of the closed state of the valve.
Figure 7B:
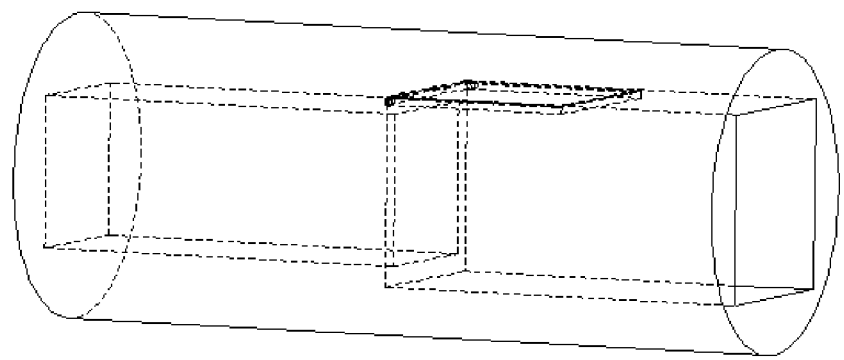
FIG. 7B is the schematic diagram of the open state of the valve.

With reference to FIGS. 7A-7B, the valve 7 includes of PDMS film 39 (95% light transmittance) and PDMS film holder 40, the top of PDMS film holder 40 is hinged to the valve body of valve 7, the PDMS film 39 is fixed on the PDMS film holder 40, the internal channel of valve 7 is changed in a stepped manner, when the airflow flows from A end to B end, the valve 7 will open automatically due to the airflow; when the airflow flows into the A end from the B end, the valve 7 is closed; the valves 7 are installed on the outsides of the manual constant-flow air pump inlet channel 8 and the manual constant-flow air pump outlet channel 10 respectively, the manual constant-flow air pump inlet channel 8 is connected to the B end of the valve 7, and the manual constant-flow air pump outlet channel 10 is connected to the A end of the valve 7; when the handle 36 is shaken clockwise, the pneumatic piston 31 will move upward, the valve 7 connected with the manual constant-flow air pump inlet channel 8 is open, the valve 7 connected with the manual constant-flow air pump outlet channel 10 is closed, at this time, the manual constant-flow air pump 9 is in the flow state; when the handle 36 is shaken counterclockwise, the pneumatic piston 31 will move downward, the valve 7 connected with the manual constant-flow air pump inlet channel 8 is closed, and the valve 7 connected with the manual constant-flow air pump outlet channel 10 is open; at this time, the manual constant-flow air pump 8 is in an outflow state.

Figure 4:
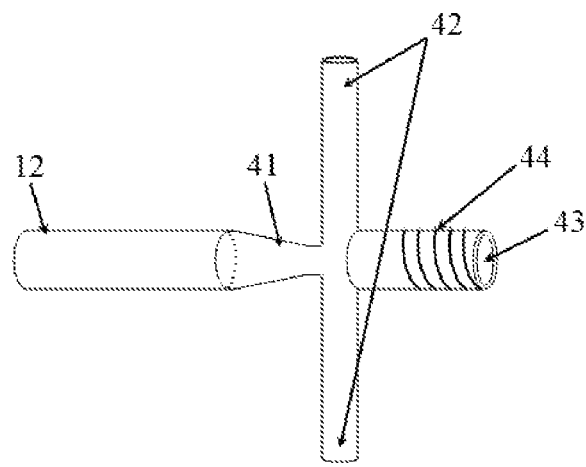
FIG. 4 is a schematic structural diagram of an impactor of the disclosure.
Figure 5A:
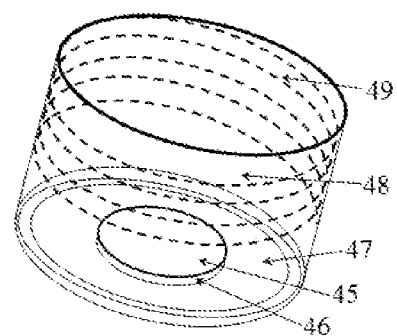
FIG. 5A is a three-dimensional schematic diagram of the airborne fungi enrichment and dyeing device.
Figure 5B:
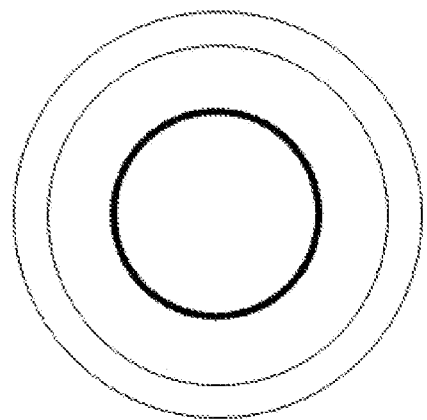
FIG. 5B is a top view of the airborne fungi enrichment and dyeing device.
Figure 5C:
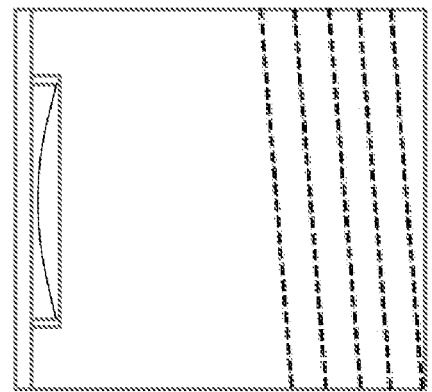
FIG. 5C is a sectional view of the airborne fungi enrichment and dyeing device.

With reference to FIG. 1 and FIG. 4, the impactor 13 includes five parts: the impactor inlet channel 12, the acceleration zone 41, the main airflow channel 42, the secondary airflow channel 43 and the interface threaded male head 44. The impactor inlet channel 12 is connected with the manual constant-flow air pump outlet channel 10 through the interface 11; airborne fungi enter the acceleration zone 41 from the impactor inlet channel 12, and air pumps are installed at both ends of the main airflow channel 42. When the manual constant-flow air pump 9 does not reach a constant state, the fungi in the air are sucked away by the air pumps. Only when the manual constant-flow air pump 9 reaches a constant state, according to the principle of inertia impact, the micro-particles with large inertia will enter the secondary airflow channel 43, and the micro-particles with small inertia will enter the main airflow channel 42 under the suction of the air pump, thus realizing the separation of the target fungi; in addition, the interface threaded male head 44 is provided outside the secondary airflow channel 43.

With reference to FIG. 1, FIG. 4 and FIGS. 5A-5C, the airborne fungi enrichment and dyeing device 14 includes five parts: reaction tank 45, reaction tank wall 46, PMMA baseplate 47, cylindrical wall 48, and interface threaded female head 49. The PMMA baseplate 47 is located at the bottom of airborne fungi enrichment and dyeing device 14, and its light transmittance can reach over 92%. The reaction tank wall 46 has a wall height of 1 mm and is located on the PMMA baseplate 47; the reaction tank 45 is the area surrounded by the reaction tank wall 46 of the reaction tank. According to the characteristics of the surface tension and wettability of the liquid, the dye can be fixed in the reaction tank 45, and the surface of the liquid is parabolic without external support.

Figure 6:
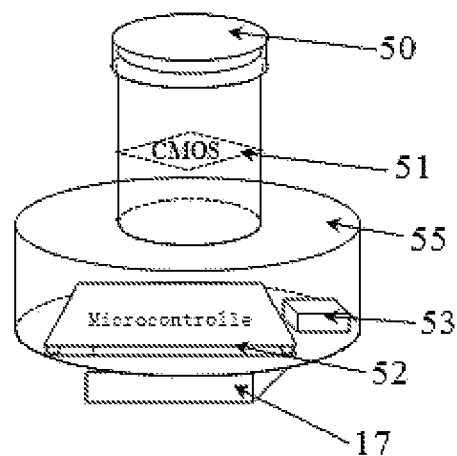
FIG. 6 is a schematic structural diagram of a fluorescence data acquiring and processing device in the disclosure.

With reference to FIG. 1 and FIG. 6, the fluorescence data acquiring and processing device 16 includes six parts: an emission filter 50, CMOS image sensor 51, a microcontroller 52, a second power supply 53, display screen 54 and detection equipment housing 55. The second power supply is a 12V power supply, and the emission filter 50 is used to screen the fluorescence emitted by airborne fungi during the fluorescence reaction in the airborne fungi enrichment and dyeing device 13. The microcontroller 52 drives the CMOS image sensor 51 to collect the image data of fluorescence reaction, and performs image processing on the collected fluorescence image data to realize quantitative detection of target fungi, and the measured data can be directly read through the data display screen 17.

With reference to FIG. 1, FIGS. 2A-2C, FIG. 3, FIG. 4, FIGS. 5A-5C, FIG. 6, FIGS. 7A-7B and FIG. 8, the specific working flow of this equipment is as follows: first, making preparations, i.e., adjusting the pneumatic piston 31 to the limit ring 37; adjusting the position of the torque adjusting bolt 35 according to the flow rate required by the detection target separation, that is, adjusting the flow rate of the manual constant-flow air pump 9; adding 20 μL of fluorescent dye to the reaction tank 45 with a pipette gun. The detection equipment is installed according to the sequence shown in FIG. 1, and the light-transmitting hole 5, the manual constant-flow air pump inlet channel 8, the manual constant-flow air pump outlet channel 10 and the reaction tank 45 are kept on the same horizontal line, so as to ensure the barrier-free propagation of the light source; Then, shake the handle 36 clockwise. At this time, the valve 7 connected with the manual constant-flow air pump inlet channel 8 is opened, and the valve 7 connected with the manual constant-flow air pump outlet channel 10 is closed. The manual constant-flow air pump 9 collects micro-particles in the air into the pump cavity 32. When the pneumatic piston 31 reaches the top of the manual constant-flow air pump 9, the handle 36 is shaken counterclockwise. At this time, the valve 7 connected with the manual constant-flow air pump inlet channel 8 is closed, and the valve 7 connected with the manual constant-flow air pump outlet channel 10 is opened. The manual constant-flow air pump 9 sends the collected micro-particles to the impactor 13 for separation at a constant speed, and finally the target airborne fungus particles are enriched in the reaction tank 45 for dyeing. 8 min later, starting the light source device 1 to stimulate the dyed fungus particles by light source to cause fluorescent reaction. Then, starting the fluorescence data collecting and processing device 16 to collect and process the dyed fluorescence images, and the relationship between fluorescence intensity and microbial concentration is quantified according to Lambert-Beer law, and the calculation results of fungi content in the air are directly displayed on the LCD (liquid crystal display) screen.

The disclosure combines the fluorescence detection technology with the gas micro particle separation technology to develop a portable airborne fungi real-time acquiring and detecting equipment. The equipment overcomes the complex and extensive collection mode in the traditional detection of airborne fungi and the demand restriction of independent detection equipment, which may realize the real-time collection and quantification of airborne fungi concentration, and the equipment has the advantages of small volume, low cost, no professional operation and is easy to be prompted.

In the description of the disclosure, it is to be understood that the terms "longitudinal", "transverse", "up", "down", "vertical", "horizontal", "top", "bottom", "inside", "outside" and the like indicate orientation or positional relationships based on those shown in the accompanying drawings and are intended only to facilitate the description of the disclosure, not to indicate or imply that the device or element referred to must have a particular orientation, be constructed and operate in a particular orientation, and therefore are not to be construed as a limitation.

The above-described embodiments only describe the preferred mode of the disclosure and do not limit the scope of the disclosure. Without departing from the design spirit of the disclosure, various modifications and improvements made by ordinary technicians in the art to the technical scheme of the disclosure shall fall within the protection scope determined by the claims of the disclosure.

What is claimed is:

1. A portable airborne fungi real-time acquiring and detecting equipment, comprising: a light source device (1), a manual constant-flow air pump (9), an impactor (13), an airborne fungi enrichment and dyeing device (14), and a fluorescence data collecting and processing device (16) sequentially connected in that order;

wherein the light source device (1) comprises a box body (18) and a light-emitting component installed in the box body (18), and the box body (18) is provided with a light-transmitting hole (5);

wherein a connecting component is arranged between the manual constant-flow air pump (9) and the box body (18), and the manual constant-flow air pump (9) is connected to the light-transmitting hole (5) through the connecting component;

wherein the manual constant-flow air pump (9) comprises a manual driver and a constant-flow piston pump in transmission connection with the manual driver, an inlet end of the constant-flow piston pump is communicated with the connecting component, an outlet end of the constant-flow piston pump is communicated with the impactor (13), valves (7) are installed on the inlet end and the outlet end of the constant-flow piston pump and between the light-transmitting hole (5) and the connecting component respectively, and light emitted by the light-emitting component is capable of passing through the connecting component, the constant-flow piston pump and the impactor (13) in sequence to irradiate the airborne fungi enrichment and dyeing device (14);

wherein the constant-flow piston pump comprises:
  a pump cavity (32);
  a manual constant-flow air pump inlet channel (8) and a manual constant-flow air pump outlet channel (10), symmetrically provided on a bottom of the pump cavity (32);
  a pneumatic piston (31), slidably disposed in the pump cavity (32);
  a pressure lever (28), fixedly connected with a middle part of a top end of the pneumatic piston (31), wherein the manual driver is in transmission connection with the pressure lever (28);
  a limit ring (37), fixedly connected with an inner wall of the pump cavity (32), wherein an end surface of a bottom of the limit ring (37) is flush with a top of the manual constant-flow air pump inlet channel (8), and the pneumatic piston (31) is matched with the limit ring (37) in positionally limiting manner;

wherein the manual driver comprises:
  brackets (26), symmetrically fixed outside the pump cavity (32);
  two three-way clamps (27), fixed at tops of the brackets (26) respectively;
  a transmission shaft (38), penetrating through the two three-way clamps (27);
  a driving gear (30), fixed on the transmission shaft (38);
  a pressure lever gear (29), fixed on the pressure lever (28), wherein the driving gear (30) is meshed with the pressure lever gear (29); and
  a handle (36), provided on an end of the transmission shaft (38);

wherein the manual driver further comprises:
  a transmission shaft friction disk (33), fixed on the end of the transmission shaft (38);
  a driving friction disk (34), arranged on one side of the transmission shaft friction disk (33) facing away from the two three-way clamps (27), wherein the driving friction disk (34) is sleeved on the transmission shaft (38); and a torque adjusting bolt (35), arranged between the driving friction disc (34) and the transmission shaft (38), wherein the driving friction disk (34) is rotatably connected with the transmission shaft (38) through the torque adjusting bolt (35), the handle (36) is perpendicularly fixed on a side wall of the driving friction disk (34), and the driving friction disk (34) is in transmission match with the transmission shaft friction disk (33);

wherein the airborne fungi enrichment and dyeing device (14) comprises a polymethyl methacrylate (PMMA) baseplate (47), a cylindrical wall (48) fixed on the PMMA baseplate (47), and a reaction tank (45) fixed in a middle of the PMMA baseplate (47);

wherein an inner side of the cylindrical wall (48) is provided with an interface threaded female head (49), and the interface threaded female head (49) is in threaded connection with the interface threaded male head (44);

wherein the fluorescence data collecting and processing device (16) comprises: a detection equipment housing (55), an emission filter (50) and a data display screen (17) both installed on the detection equipment housing (55), a complementary metal oxide semiconductor (CMOS) image sensor (51), a microcontroller (52), and a second power supply (53);

wherein a connector (15) is installed at an end of the detection equipment housing (55) close to the emission filter (50), and the detection equipment housing (55) is connected with the airborne fungi enrichment and dyeing device (14) through the connector (15); and wherein the emission filter (50) is located between the detection equipment housing (55) and the airborne fungi enrichment and dyeing device (14), the CMOS image sensor (51) is arranged between the emission filter (50) and the detection equipment housing (55), the microcontroller (52) and the second power supply (53) are installed in the detection equipment housing (55); the CMOS image sensor (51), the data display screen (17) and the second power supply (53) are electrically connected to the microcontroller (52); and the data display screen (17) is fixed on a side wall of the detection equipment housing (55) facing away from the CMOS image sensor (51);

wherein the light-emitting component comprises a circuit fixing bracket (20), a white light-emitting diode (23), a first power supply (19) and an excitation filter device (22), a wire, a circuit protection layer (21), a power button (2), a shading plate (4), an excitation filter (24) and a light-transmitting protective layer (25);

wherein the white light-emitting diode (23) is electrically connected with the first power supply (19) through the wire, an outer side of the wire is covered with the circuit protection layer (21), the white light-emitting diode (23) is fixedly matched with the circuit fixing bracket (20) through the circuit protection layer (21), the white light-emitting diode (23) horizontally corresponds to the light-transmitting hole (5);

wherein the power button (2) is connected in series on the wire and fixed outside the box body (18);

wherein the shading plate (4) is fixed on one side of the box body (18) close to the manual constant-flow air pump (9), and the light-transmitting hole (5) is arranged on the shading plate (4); and wherein the excitation filter device (22) is arranged between the shading plate (4) and the white light emitting diode (23), and the excitation filter device (22) comprises an excitation filter holder (3) detachably connected with the box body (18), the excitation filter holder (3) is detachably connected with the excitation filter (24) and the light-transmitting protective layer (25), and the light-transmitting protective layer (25) is located between the excitation filter (24) and the shading plate (4);

the connecting component comprises a connecting pipe (6), a T-joint (56) and a suction hose (57);

wherein one end of the connecting pipe (6) is communicated with the light-transmitting hole (5), and the other end of the connecting pipe (6) is provided with one of the valves (7);

wherein two ports in a horizontal direction of the T-joint (56) are respectively communicated with the one of the valves (7) on the connecting pipe (6) and another one of the valves (7) on the inlet end of the constant-flow piston pump, and the suction hose (57) is communicated with a port in a perpendicular direction of the T-joint (56).

* * * * *